United States Patent [19]

Smith et al.

[11] Patent Number: 5,399,591

[45] Date of Patent: Mar. 21, 1995

[54] SUPERABSORBENT POLYMER HAVING IMPROVED ABSORPTION RATE AND ABSORPTION UNDER PRESSURE

[75] Inventors: Scott J. Smith, Aurora; Eric J. Lind, Naperville, both of Ill.

[73] Assignee: Nalco Chemical Company, Naperville, Ill.

[21] Appl. No.: 181,931

[22] Filed: Jan. 18, 1994

Related U.S. Application Data

[62] Division of Ser. No. 123,561, Sep. 17, 1993, Pat. No. 5,314,420.

[51] Int. Cl.⁶ .................. C08J 9/232; C08J 9/236; C08J 9/33
[52] U.S. Cl. .................. 521/53; 521/54; 521/64; 521/149
[58] Field of Search ............ 521/64, 53, 54, 149

[56] References Cited

U.S. PATENT DOCUMENTS

| | | | |
|---|---|---|---|
| 4,666,983 | 5/1987 | Tsubakimoto et al. | 525/119 |
| 4,824,901 | 4/1989 | Alexander et al. | 524/555 |
| 5,102,597 | 4/1992 | Roe et al. | 521/142 |
| 5,118,719 | 6/1992 | Lind | 521/92 |
| 5,124,188 | 6/1992 | Roe et al. | 521/919 |
| 5,140,076 | 8/1992 | Hatsuda et al. | 525/375 |
| 5,145,906 | 9/1992 | Chamber et al. | 524/732 |
| 5,154,713 | 10/1992 | Lind | 604/358 |
| 5,229,466 | 7/1993 | Brehm et al. | 526/317.1 |
| 5,300,565 | 4/1994 | Berg et al. | 525/54.2 |

FOREIGN PATENT DOCUMENTS 649240 5/1994 Australia .
4020780 8/1991 Germany .

*Primary Examiner*—Morton Foelak
*Attorney, Agent, or Firm*—Robert A. Miller; James J. Drake

[57] ABSTRACT

A superabsorbent polymer having improved absorption under pressure and fast absorption rate is obtained by first providing a solution containing carboxylic acid monomers or water soluble salts thereof, and a crosslinking agent. A carbonate blowing agent and a polymerization initiator are added, individually or in combination, to the solution to form a carbonated monomer solution. A polymerization initiator is then added to the carbonated monomer solution which is then polymerized at temperatures ranging from about 0° C. to about 130° C., forming a microcellular hydrogel. The microcellular hydrogel is chopped or ground into gel pieces having a particle diameter ranging from about 0.1 mm to about 5.0 cm. The gel pieces are dried at temperatures ranging from about 85° C. to about 210° C., and are then ground to form a polymer having a particle size of from about 0.05 mm to about 5.0 mm. A mixture is formed from 100 parts by weight of the polymer and about 0.001 to about 30 parts by weight of a surface crosslinking agent. The polymer is reacted with the surface crosslinking agent to crosslink molecular chains existing on a surface of the polymer, forming the superabsorbent polymer.

13 Claims, No Drawings

SUPERABSORBENT POLYMER HAVING IMPROVED ABSORPTION RATE AND ABSORPTION UNDER PRESSURE

This application is a division of Ser. No. 08/123,561, filed Sep. 17, 1993, now U.S. Pat. No. 5,314,420.

FIELD OF THE INVENTION

The present invention relates generally to superabsorbent polymers exhibiting improved absorption under pressure and fast absorption rates. This invention particularly relates to providing a surface crosslinked superabsorbent polymer which incorporates a blowing agent.

BACKGROUND OF THE INVENTION

Superabsorbent polymers are water insoluble, hydrogel-forming polymers capable of absorbing large quantities of aqueous fluids including synthetic urine, brines, and biological fluids such as urine, sweat, and blood, while retaining the absorbed fluids under pressure. Hydrogel-forming superabsorbent polymers are useful as absorbents for water and aqueous body fluids when the polymers are incorporated in absorbent articles, such as disposable diapers, adult incontinence pads, sanitary napkins, and bandages. Many of the existing superabsorbents are formed from unsaturated carboxylic acid monomers including acrylic acid, methacrylic acid, alkylacrylates, and acrylamides which are rendered water insoluble by crosslinking.

The degree of crosslinking affects the absorbent capacity and gel strength of a superabsorbent. Capacity is a measure of the amount of fluid which a given amount of superabsorbent polymer will absorb. Gel strength indicates the tendency of the hydrogel once formed to deform under an applied stress. Polymers exhibiting inadequate gel strength will form a hydrogel which deforms and fills the void space in an absorbent article, inhibiting absorbent capacity and fluid distribution throughout the article. Polymers having low absorbent capacity are incapable of absorbing a sufficient amount of the fluid encountered in use of a diaper or other absorbent article. A polymer having a high gel strength generally possesses a low absorption capacity, and a polymer having a high absorption capacity typically possesses a low absorption rate because of gel blocking phenomenon or low gel strength after absorption.

Another characteristic that a superabsorbent polymer must possess is an acceptable level of extractable, water soluble polymer remaining within the superabsorbent. The extractable polymer can leach out of a hydrogel when fluids contact the superabsorbent. The extractables that leach out of the superabsorbent apparently lower the absorption speed and capacity of the superabsorbent, resulting in leakage of the fluid from an absorbent article.

Commercially available superabsorbents generally possess sufficient capacity, but do not have adequate gel strength, swell rate (i.e., absorption speed) and absorption under pressure for the absorbent articles of reduced size and thickness that are now being produced. As fluff fiber in absorbent products is replaced with greater amounts of superabsorbent polymer, the polymer has to perform the functions of the fluff fiber. The polymer must quickly absorb fluid and transport it throughout an absorbent! article without releasing the stored fluid from the swelled hydrogel on exertion of pressure. Accordingly, the swollen gel particles cannot impede absorption of additional fluid by forming a barrier, but must maintain their liquid permeability.

In order to improve the absorption speed of superabsorbent polymers, blowing agents have been incorporated into superabsorbents as described in U.S. Pat. Nos. 5,118,719 and 5,145,713. As the blowing agent is dispersed throughout the monomer solution during polymerization, it releases carbon dioxide when heated. The porosity of the resultant superabsorbent polymer provides more surface area within the polymer particles, increasing the rate at which fluid is absorbed by the polymer.

The absorption under pressure of a superabsorbent has been improved by crosslinking the molecular chains at the surface of the polymer. Surface crosslinkage also improves the gel strength of the polymer and reduces the amount of extractables at the polymer surface. Although capacity is reduced at the polymer surface, the core of the polymer, which has lower crosslink density, retains its absorbance capacity. Crosslinking at the surface of the polymer particles provides spacings between the particles when swelled, allowing fluid to pass the swelled particles and travel throughout the absorbent article. Surface crosslinkage, however, frequently reduces the absorption speed of the polymer. While these materials possess adequate absorption under pressure, they absorb significantly slower than the fluff fiber they are replacing in thinner personal care articles.

The polymers which have been crosslinked at their surface (herein referred to as core polymers) are not porous materials like those disclosed in U.S. Pat. Nos. 5,118,719 and 5,145,713. Accordingly, these superabsorbents generally exhibit slow rates of absorption. U.S. Pat. Nos. 4,666,983 and 5,140,076 disclose absorbent polymers formed from reacting an absorbent resin powder having a carboxyl group with a crosslinking agent having at least two functional groups per molecule to crosslink the surface of the polymer. German Patent No. 4,020,780 describes surface crosslinked superabsorbent particles formed by coating monomers having acid groups with an alkylene carbonate. U.S. Pat. No. 5,229,466 discloses surface crosslinking by treating a water swellable carboxyl group containing polymer with a solution of an N-(hydroxyalkyl)-beta-(meth)-alanine ester or a polycondensation product thereof. A superabsorbent polymer made from acrylic acid, a water soluble polysaccharide and a crosslinking monomer having at least two polymerizable ethylenically unsaturated double bonds per molecule is described in U.S. Pat. No. 5,145,906. Water absorbent resins surface treated with a polyquaternary amine are disclosed in U.S. Pat. No. 4,824,901.

There is a need for a method of producing a water absorbent resin which exhibits high absorbency under pressure, high absorption speed and high gel strength.

SUMMARY OF THE INVENTION

In order to satisfy the need for improved superabsorbents having greater absorption under pressure and fast absorption rate, one aspect of the present invention provides a superabsorbent polymer preparable by the process of first providing a solution containing carboxylic acid monomers or water soluble salts thereof, and a crosslinking agent, herein referred to as the monomer solution. A carbonate blowing agent and a polymerization initiator are added, individually or in combination, to the monomer solution to form a carbonated monomer solution. The carbonated monomer solution is then polymerized at temperatures ranging from about 0° C. to about 130° C., forming a microcellular hydrogel. The microcellular hydrogel is chopped or ground into gel pieces having a particle diameter ranging from about 0.1 mm to about 5.0 cm. The gel pieces are dried at temperatures ranging from about 85° C. to about 210° C., and are then ground to form a polymer having a particle size of from about 0.05 mm to about 5.0 mm. A mixture is formed from 100 parts by weight of the polymer and about 0.001 to about 30 parts by weight of a surface crosslinking agent. The polymer is reacted with the surface crosslinking agent to crosslink molecular chains existing on a surface of the polymer, forming the superabsorbent polymer.

Another embodiment of the present invention is a method of making a superabsorbent polymer having improved absorption under pressure and absorption rate when absorbing aqueous body fluids by the above identified process.

A third embodiment of the invention is a method of improving the absorption under pressure and absorption rate of a superabsorbent polymer. The superabsorbent polymer is made by the method as described above, and is then exposed to aqueous body fluids, when the superabsorbent polymer is under the exertion of pressure. The superabsorbent polymer can be contained within a diaper, an incontinence pad, a sanitary napkin or a bandage.

It is an object of this invention to provide a surface crosslinked superabsorbent polymer which exhibits improved absorption under pressure while increasing the absorption rate of the polymer with or without an applied pressure.

An associated object of the invention is to provide a superabsorbent polymer having a core with a lower crosslink density as compared to the surface of the polymer such that the core retains its absorbance capacity.

Another object of the invention is to provide a superabsorbent polymer in which spacings exist between the polymer particles when swelled, allowing fluid to pass the swelled particles and travel throughout the absorbent article.

Yet another object of the invention is to provide superabsorbent polymer particles with better bulk, inter- and intra-particle permeability.

Other objects will be apparent to those skilled in the art from the disclosure herein.

DETAILED DESCRIPTION OF THE INVENTION

The present invention provides a hydrogel-forming superabsorbent polymer which can be incorporated in absorbent articles such as diapers, adult incontinence pads, sanitary napkins, and bandages. The polymer can be used to effectively replace fluff fiber within these products because the polymer quickly absorbs fluid and transports it throughout the product without releasing the stored fluid from the swelled hydrogel on exertion of pressure. The swollen gel particles do not impede absorption of additional fluid by forming a barrier, but maintain their liquid permeability.

The superabsorbent polymer of the present invention may be prepared by first forming a monomer solution containing carboxylic acid monomers or water soluble salts thereof, and an effective water insolubilizing amount of a crosslinking agent. A carbonate blowing agent and a polymerization initiator are added, individually or in combination, to the monomer solution to form a carbonated monomer solution. The carbonated monomer solution is then polymerized to form a microcellular hydrogel. The microcellular hydrogel is chopped or ground into gel pieces which are then dried and ground to form a core polymer.

After the core polymer is made, it is surface crosslinked to provide superabsorbent particles having a low crosslink density within the particle core and a high crosslink density on the surface of the particle. A mixture is formed from 100 parts by weight of the core polymer and about 0.001 to about 30 parts by weight of a surface crosslinking agent. The core polymer is reacted with the surface crosslinking agent to crosslink molecular chains existing on a surface of the core polymer, forming the superabsorbent polymer.

More specifically, the core polymer is formed in solution, or in a water-in-oil emulsion containing carboxylic acid containing monomers and a crosslinking agent. An effective microcellular forming amount of the carbonate blowing agent is added to the monomer solution to form the carbonated monomer solution.

A polymerization initiator is added to the monomer solution or the carbonated monomer solution for the purpose of initiating the reaction between the monomers and the crosslinking agent. The initiator is either added to the monomer solution immediately before or simultaneously with addition of the blowing agent, or is added to the carbonated monomer solution immediately after the blowing agent has been added to the monomer solution. The initiator is added within no more than five minutes before, or fifteen minutes after the addition of the carbonate blowing agent to the monomer solution. Simultaneous addition of both initiator and blowing agent, or addition of initiator after the addition of blowing agent is preferred.

The core polymer is preferably formed from a thin layer of the carbonated monomer solution, which has been deaerated (purged of oxygen). The thin layer solution is preferably deaerated and protected from air before polymerization, and after initiating polymerization by the addition of free radical catalysts or by ionizing radical forming radiation. The polymerization forms an aqueous hydrogel of the crosslinked, water insoluble core polymer. The polymerization is exothermic, causing the gel temperature to increase from the initial temperature of the carbonated monomer solution of about 0° C. to 20° C. to temperatures of about 80° C. to 130° C. The aqueous gel, in the presence of the carbonate blowing agent, develops a microcellular hydrogel as polymerization occurs because decomposition of the carbonate blowing agent upon heating disperses carbon dioxide throughout the hydrogel.

The microcellular structure of the core polymer may appear cloudy (demonstrating relatively small dispersed gas bubbles), opaque (normally representing somewhat larger gas bubbles or higher quantities of carbon dioxide), or foamy. The microcellular gel volume increases range from about 1.01 to at least 10.0 times the volume of the carbonated monomer solution, primarily depending upon the concentration of the carbonate blowing agent contained in the carbonated monomer solution.

The microcellular gel is then masticated by chopping, grinding, or otherwise forming gel pieces have particle diameter sizes ranging from about 0.1 millimeter to about 5.0 centimeters, preferably about 10 millimeters to about 2.0 centimeters. These masticated gel pieces are then dried at temperatures ranging from about 85°

C. to about 210° C. to form a dry superabsorbent core polymer. The core polymer is then ground to a particle size having a diameter of from about 0.05 millimeter to about 5.0 millimeters. The resultant core polymer as described in U.S. Pat. Nos. 5,154,713 and 5,118,719, which are incorporated herein by reference, exhibits an improved rate of absorption of aqueous fluids while essentially retaining the gel strength and capacity of conventional superabsorbents made without carbonate blowing agents.

After the core polymer is formed, the surface region of the core polymer is crosslinked using a surface crosslinking agent to obtain the superabsorbent polymer of the present invention. Surface crosslinking of the core polymer improves the absorption under pressure, absorption rate, and gel strength after absorption while maintaining an acceptable absorption capacity. The surface crosslinking agents for use in the present invention include organic carbonates, polyquaternary amines, multivalent cations and compounds possessing in the molecular unit thereof at least two functional groups capable of reacting with the carboxyl group of the core polymer. 100 parts by weight of the core polymer formed as described above are mixed with about 0.01 to about 30 pans by weight of a surface crosslinking agent, depending upon the selected core polymer, and the surface region of the core polymer is reacted with the surface crosslinking agent. The reaction can be carried out during and/or after mixing using a conventional mixer.

The reaction between the core polymer and the surface crosslinking agent may occur at room temperature as when an aziridine compound is selected as the surface crosslinker. Heat is preferably applied to promote the reaction although it is not required to effect the reaction in many instances. When heat must be applied for the reaction to occur as when a polyhydric alcohol, a polyglycidyl compound, a polyamine compound, or a polyoxazoline compound is used as the surface crosslinking agent, the heat is preferably applied after the core polymer and the surface crosslinking agent have been mixed. The temperature of the heat treatment is generally in the range of 40° C. to 250° C., preferably in the range of 90° C. to 250° C. At temperatures exceeding 250° C., the core polymer could be subject to thermal deterioration. The mixture can be heated using conventional dryers or heating ovens.

The materials required to produce the superabsorbent polymers of the invention are specified below. The core polymer is formed using monomers in an aqueous solution, or monomers dissolved in water and then dispersed in a water-in-oil emulsion. The hydrogel-forming core polymer is normally synthesized from aqueous solutions containing acrylic acid, methacrylic acid, their water soluble salts, and mixtures thereof. The monomers are preferably dissolved in an aqueous solution containing the crosslinking agent. The monomer solution contains at least 20 percent by weight total monomer content, preferably about 25 to about 75 percent by weight total monomer content, and most preferably from about 30 to about 60 percent by weight total monomer content.

Any olefinically unsaturated carboxylic acid and carboxylic acid anhydride monomers can be used to form the core polymer of the invention. Suitable monomers include acrylic acids and their anhydrides such as acrylic acid, methacrylic acid, ethacrylic acid, alpha-chloroacrylic acid, alphacyanoacrylic acid, and beta-methyl acrylic acid. For purposes of the present invention, the term (meth)acrylic acid represents the presence of acrylic acid alone, methacrylic acid alone, any admixture of these acids, and any water soluble salt of these acids, either alone or in admixture. The unsaturated carboxylic acid monomers can also include itaconic acid, citraconic acid, maleic acid, fumaric acid, and maleic anhydride. Other olefinic unsaturated monomers can also be used, such as the sulfonic acid monomers. These monomers can be chosen from, but are not limited to, vinyl sulfonic acids, allyl sulfonic acids, styrene esters including sulfoacrylic and methacrylic acid esters such as sulfoethylacrylate, sulfoethylmethacrylate, sulfopropylacrylate, and sulfopropylmethacrylate, and sulfo(meth)acrylamide materials such as acrylamido N-methylene sulfonic acid, acrylamido-N-ethylene sulfonic acid, and 2-acrylamido-2-methylpropane sulfonic acid. Other olefinically unsaturated monomers such as acrylamide and methacrylamide are useful in forming copolymers which can be crosslinked to form a core polymer.

The monomers are preferably selected from the group consisting of acrylic acid, the water soluble salts of acrylic acid, methacrylic acid, the water soluble salts of methacrylic acid, and mixtures thereof. A preferred monomer mixture consists essentially of from 20 weight percent to 40 weight percent (meth)acrylic acid and from 60 weight percent to 80 weight percent sodium (meth)acrylate.

The core polymer is made from free acid, partially neutralized monomers, or is partially or completely neutralized either before or after polymerization by addition of appropriate base materials, such as sodium hydroxide, ammonia, and the like. Any suitable basic salt forming cation including the alkaline metals, ammonia, ammonium salts, and amines may be used for the purpose of neutralization.

It is preferred to have a degree of neutralization of the carboxylic acid monomers of at least 50 mole percent and up to about 60 to 80 mole percent. When appropriate, the degree of neutralization can be partially accomplished by the addition of the carbonate blowing agents.

Preferably, the carboxyl group is present in the core polymer in an amount of not less than 0.01 equivalent, based on 100 g of the core polymer. In the case of a partially neutralized polyacrylic acid, for example, the proportion of the unneutralized polyacrylic acid is preferably in the range of 1 to 50 mole percent, preferably 5 to 40 mole percent.

The crosslinking agents that can be used to form the monomer solution include, but are not limited to, compounds having at least two polymerizable double bonds, compounds having at least one polymerizable double bond and at least one functional group reactive with the acid containing monomer material, compounds having at least two functional groups reactive with the acid containing monomer material, and polyvalent metal compounds, which metallic cations can form ionic crosslinkages. Crosslinking agents containing at least two polymerizable double bonds include di, tri or polyvinyl compounds such as divinyl benzene and divinyl toluene, di, tri or polyesters of unsaturated mono or poly carboxylic acids with polyols including di or tri acrylic acid esters of polyols such as ethylene glycol, trimethylpropane, glycerine, and polyoxyethylene glycols. Other crosslinking agents can include alkylene bis-acrylamides such as N,N'-methylene-bis-acrylamide, carbamyl esters obtained by reacting polyisocyanates with hydroxyl group containing monomers, di, tri or poly allyl esters of polyols, di, tri or poly allyl esters of polycarboxylic acids such as diallyl phthalate and diallyl adipate, poly carboxylic acid polyols such as trimethylolpropane triacrylate, esters of unsaturated mono or poly-carboxylic acids with monoallyl esters of polyols such as the acrylic acid ester of polyethylene glycol monoallyl ether, and di or triallyl amine, and the alkylene glycol diglycidyl ethers.

The crosslinking agent is present in an amount ranging from about 0.005 weight percent of the monomer solution to about 2.0 weight percent of the monomer solution. Preferably, the crosslinking agent is used in an amount ranging from about 0.10 weight percent to about 1.0 weight percent based on the weight of the monomer solution.

The most preferred crosslinking agents are bis-acrylamides such as N-N'-methylene bis-acrylamide, the di, tri or polyesters of unsaturated mono or poly carboxylic acid polyols such as trimethylolpropane triacrylate, the di or tri glycidyl ethers of polyols such as ethylene glycol diglycidyl ether, the multi-substituted allyl amines such as diallyl amine and triallyl amine, or mixtures thereof.

Carbonate blowing agents are added to the monomer solution to form the carbonated monomer solution. The blowing agent releases carbon dioxide when heated while dissolved or dispersed in the carbonated monomer solution. The blowing agent can be any carbonate or bicarbonate containing salt or mixed salt, and may include carbon dioxide as a gas or a solid, sodium carbonate, potassium carbonate, ammonium carbonate, magnesium carbonate, or magnesium (hydroxic) carbonates, calcium carbonate, barium carbonate, bicarbonates and their hydrates, or other cations, as well as naturally occurring carbonates, such as dolomite, and mixtures thereof. Preferred carbonate blowing agents are $MgCO_3$, $(NH_4)_2CO_3$, $Na_2CO_3$, and mixtures thereof.

It is preferred to add from about 0.05 to about 2.5 weight percent blowing agent based on the weight of the carbonated monomer solution. It is most preferred to add from about 0.2 weight percent to about 2.5 weight percent blowing agent. The blowing agents must be added before or immediately after polymerization is initiated. The blowing agents are not effective if added after the hydrogel is formed, nor is it effective when added after chopping or drying the gelled polymer.

The preferred blowing agents are carbonate salts of multivalent cations such as magnesium, calcium, and zinc. Although many of the multivalent transition metal cations can be used, some of them, such as ferric cation, can cause color staining and may be subject to reduction-oxidation reactions or hydrolysis equilibria in water. This may lead to difficulties in quality control of the final polymeric product. Also, other multi-valent cations such as nickel, barium, cadmium, and mercury would be unacceptable because of potential toxic off skin sensitizing effects.

The polymerization of the carbonated monomer solution is initiated with free radical catalysts which are well known in the art. These initiators may include, but are not limited to, peroxide or persulfate catalysts, azo catalysts, the so called redox catalysts, or any combination thereof. Preferred catalysts include hydrogen peroxide, sodium persulfate, organic peroxides, sodium bisulfite, peracetate catalysts, azo catalysts and mixtures thereof.

The surface crosslinking agents for use in the present invention include organic carbonates, polyquaternary amines, polyvalent metal compounds and compounds possessing in the molecular unit thereof at least two functional groups capable of reacting with the carboxyl group of the core polymer. The surface crosslinking agents include polyhydric alcohols such as ethylene glycol, diethylene glycol, triethylene glycol, tetraethylene glycol, polyethylene glycol, glycerin, polyglycerol, propylene glycol, diethanolamine, triethanolamine, polyoxypropylene, oxyethylene-oxypropylene block copolymer, sorbitan fatty acid esters, polyoxyethylene sorbitan fatty acid esters, trimethylolpropane, pentaerythritol, polyvinyl alcohol and sorbitol, polyglycidyl ether compounds such as ethylene glycol diglycidyl ether, polyethylene glycol diglycidyl ether, glycerin diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and polypropylene glycol diglycidyl ether, polyaziridine compounds such as 2,2-bishydroxymethylbutanoltris[3-(1-aziridinyl)propionate], 1,6-hexamethylene diethylene urea, and diphenylmethane-bis-4,4'-N,N'-diethylene urea, haloepoxy compounds such as epichlorohydrin and α-methylfluorohydrin, polyamine compounds such as ethylene diamine, diethylene triamine, triethylene tetramine, tetraethylene pentamine, pentaethylene hexamine, and polyethylene imine, polyisocyanate compounds such as 2,4-tolylene diisocyanate and hexamethylene diisocyanate, hydroxides of zinc, calcium, magnesium, aluminum, iron, titanium and zirconium, halogenides, alkylene carbonates such as 1,3-dioxolan-2-one and 4-methyl-1,3-dioxolan-2-one, polyvalent metal compounds such as salts, (represented by sulfates), for example, and polyquaternary amines such as condensation products of dimethylamine and epichlorohydrin, homo and copolymers of diallyldimethyl ammonium chloride, and homo and copolymers of dimethylaminoethyl(meth)acrylate methyl chloride quaternary ammonium salts. One crosslinking agent or two or more mutually unreactive crosslinking agents selected from the group mentioned above are used.

Preferably, the surface crosslinking agent includes at least one compound selected from the group consisting of diethylene glycol, triethylene glycol, polyethylene glycol, glycerin, polyglycerin, propylene glycol, diethanolamine, triethanolamine, polyoxypropylene, oxyethylene-oxypropylene block copolymer, sorbitan fatty acid esters, polyoxyethylene sorbitan fatty acid esters, trimethylol propane, pentaerythritol, polyvinyl alcohol, sorbitol, ethylene carbonate, and ethylene glycol diglycidyl ether. The crosslinking agent is used in an amount ranging from about 0.01 to about 30 parts by weight, preferably about 0.1 to about 10 parts by weight, based upon 100 parts by weight of the core polymer.

Organic solvents or water can be added as the core polymer and the surface crosslinking agent are mixed to promote uniform dispersion. The amount of water to be used is in the range of 0 to about 50 parts by weight, preferably up to about 40 parts by weight, more preferably up to about 20 parts by weight, based upon 100 parts by weight of the core polymer. If the amount of water exceeds 50 parts by weight, drying time is increased and the surface crosslinking agent permeates to the center of the core polymer particles, reducing the absorption capacity.

Organic solvents can be added to the mixture in an amount of 0 to about 60 parts by weight, preferably up to about 10 parts by weight, based upon 100 parts by weight of the core polymer. Amounts of solvent in excess of 60 parts by weight increase the required drying time of the superabsorbent. The organic solvents include lower alcohols such as methanol, ethanol, n-propanol, isopropanol, n-butanol, isobutanol, sec-butanol, and t-butanol, ketones such as acetone, methylethyl ketone and methylisobutyl ketone, ethers such as dioxane, tetrahydrofuran and diethyl ether, amides such as N,N-dimethyl formamide and N,N-diethyl formamide, and sulfoxides such as dimethyl sulfoxide.

Absorbent articles such as diapers, adult incontinence pads, sanitary napkins and bandages may have a core entirely composed of the superabsorbent polymer of the present invention, or can include polymer layers comprised of up to 100% of the superabsorbent polymer within the core material.

The following examples are presented to describe preferred embodiments and utilities of the present invention and are not meant to limit the present invention unless otherwise stated in the claims appended hereto.

EXAMPLE 1

The following test methods were performed to determine the characteristics of the tested polymers. Absorption under pressure (AUP) is determined by first placing a glass fritted plate inside a crystallizing dish. The dish is filled with 0.9 wt. % saline or synthetic urine to the top level of the filter plate and a piece of Whatman filter paper #1 is placed on top of the plate. 0.9000 grams of polymer is distributed evenly over a 400 mesh screen fixed to the bottom of a plastic cylinder. A teflon plunger and a weight exerting 0.3 or 0.7 psi is placed inside the cylinder and the entire cylinder assembly is weighed. The cylinder assembly is placed on the filter plate and allowed to absorb fluid for a specified time and then reweighed. The level of fluid in the dish is kept constant during absorption. The absorption under pressure is calculated by dividing the difference in the complete cylinder apparatus weight before and after absorption by the dry weight of the polymer.

Centrifuge capacity is calculated by placing $0.2000 \pm 0.005$ grams of polymer in a tea bag and sealing the bag. The bag is then placed in 0.9% saline or synthetic urine along with blanks (empty bags) and is allowed to absorb for a specified time. The tea bags are removed from the test liquid and centrifuged at 1500 rpm for three minutes. The weight of the tea bags and blanks is recorded. The absorptive centrifuge capacity is calculated by subtracting the weight of the blank and the dry polymer from the weight of the wet bag containing polymer, and dividing that amount by the dry polymer weight.

Swell rate is determined by screening $0.358 \pm 0.001$ grams polymer to a $-20/+50$ mesh particle size, weighing the polymer and placing it in a 16 mm test tube. 10.0 ml of synthetic urine is added to the tube at time zero. The time required for the gel to swell to the bottom of the fluid meniscus is recorded. The swell rate is calculated by dividing the volume of fluid absorbed by the mass of the polymer used and the time required to absorb the fluid.

The synthetic urine tested contains the following cations and anions or elements dissolved in water: 600–700 ppm $Na^+$, 65–75 ppm $Ca^{2+}$, 55–65 ppm $Mg^{2+}$, 1100–1200 ppm $K^+$, 240–280 ppm phosphorus, 450–500 ppm sulfur, 1100–1300 ppm chloride, and 1300–1400 ppm sulfate.

Aqueous monomer solutions containing about 30 to 40 weight percent of a combination of acrylic acid and sodium acrylate in a ratio of about 30:70 and triallyl amine crosslinking agent in the amounts specified in Table 1 were formed. The samples were polymerized without incorporation of a blowing agent. The resultant gel was ground and dried, and the characteristics of the nonporous core polymer were measured using the tests described above for determining gel strength, capacity and swell rate. These results are reported as samples 1 and 3 in Table 1. The nonporous core polymers of samples 1 and 3 were then surface crosslinked by reacting the polymers with from about 1 to about 3 weight percent ethylene carbonate to form the superabsorbent polymers of samples 2 and 4, respectively. The gel strength, capacity and swell rate for the samples are listed below:

TABLE 1

| Sample | Swell Rate (g/g sec) | Gel Strength (dynes/cm²) | Capacity (g/g) | AUP @ 5 mins. (g/g) | AUP @ 60 mins. (g/g) |
| --- | --- | --- | --- | --- | --- |
| 1: 900 ppm crosslinker, no blowing agent | 0.21 | 33,535 | 47.9 | 4.3 (.3 psi)<br>4.1 (.7 psi) | 8.4 (.3 psi)<br>7.7 (.7 psi) |
| 2: surface crosslinked sample 1 | 0.17 | 55,400 | 39.7 | 26.1 (.3 psi)<br>17.0 (.7 psi) | 33.1 (.3 psi)<br>20.4 (.7 psi) |
| 3: 2500 ppm crosslinker, no blowing agent | 0.28 | 77,310 | 35.6 | 6.5 (.3 psi)<br>4.4 (.7 psi) | 22.4 (.3 psi)<br>9.0 (.7 psi) |
| 4: surface crosslinked Sample 3 | 0.23 | 99,100 | 30.0 | 29.6 (.3 psi)<br>24.7 (.7 psi) | 34.9 (.3 psi)<br>28.9 (.7 psi) |

After the surfaces of the nonporous core polymers were crosslinked, the swell rate and capacity were reduced while the gel strength and absorption under pressure substantially improved.

EXAMPLE 2

Aqueous monomer solutions containing about 30 to 40 weight percent of a combination of acrylic acid and sodium acrylate in a ratio of about 30:70 and triallyl amine crosslinking agent in the amounts specified in Table 2 were formed. The samples were polymerized without incorporation of a blowing agent. The resultant gel was ground and dried, and the characteristics of the nonporous core polymer were measured using the tests described above for determining gel strength, capacity and swell rate. These results are reported as samples 1, 3 and 5 in Table 2. The nonporous core polymers of samples 1, 3 and 5 were then surface crosslinked by reacting the polymers with from about 3 weight percent glycerol to form the superabsorbent polymers of samples 2, 4 and 6, respectively. The gel strength and swell rate for the samples are listed below:

TABLE 2

| Sample | Swell Rate (g/g sec) | Gel Strength (dynes/cm²) |
| --- | --- | --- |
| 1: 900 ppm crosslinker, no blowing agent | 0.20 | 60,360 |

TABLE 2-continued

| Sample | Swell Rate (g/g sec) | Gel Strength (dynes/cm$^2$) |
|---|---|---|
| 2: Surface crosslinked Sample 1 | 0.27 | 58,815 |
| 3: 1500 ppm crosslinker, no blowing agent | 0.21 | 62,910 |
| 4: Surface crosslinked Sample 3 | 0.33 | 66,785 |
| 5: 1500 ppm crosslinker, no blowing agent | 0.27 | 67,230 |
| 6: Surface crosslinked Sample 5 | 0.39 | 69,015 |

After the surfaces of the nonporous core polymers were crosslinked, the swell rate unexpectly improved, and the gel strength improved.

EXAMPLE 3

Aqueous monomer solutions containing about 30 to 40 weight percent of a combination of acrylic acid and sodium acrylate in a ratio of about 30:70 and triallyl amine crosslinking agent in the amounts specified in Table 3 were formed. 0.4 weight percent $Na_2CO_3$ blowing agent was added to the monomer solution, forming a carbonated monomer solution. The samples were polymerized and the resultant microcellular gel was ground and dried. The characteristics of the porous core polymer were measured using the tests described above for determining gel strength, capacity and swell rate. These results are reported as samples 1, 3 and 5 in Table 3. The porous core polymers of samples 1, 3 and 5 were then surface crosslinked by reacting the polymers with from about 1 to about 3 weight percent glycerol to form the superabsorbent polymers of samples 2, 4 and 6, respectively. The gel strength, capacity and swell rate for the samples are listed below:

TABLE 3

| Sample | Swell Rate (g/g sec) | Gel Strength (dynes/cm$^2$) | Capacity (g/g) | AUP @ 5 mins. (g/g) | AUP @ 60 mins. (g/g) |
|---|---|---|---|---|---|
| 1: 1,400 ppm crosslinker, blowing agent | 0.49 | 48,845 | 42.5 | 4.8 (.3 psi) 4.0 (.7 psi) | 10.2 (.3 psi) 8.0 (.7 psi) |
| 2: Surface crosslinked Sample 1 | 0.57 | 69,760 | 35.5 | 30.6 (.3 psi) 11.4 (.7 psi) | 37.5 (.3 psi) 20.4 (.7 psi) |
| 3: 2,000 ppm crosslinker, blowing agent | 0.47 | 67,470 | 39.1 | 5.1 (.3 psi) 4.1 (.7 psi) | 12.9 (.3 psi) 8.2 (.7 psi) |
| 4: Surface crosslinked Sample 3 | 0.58 | 79,245 | 33.1 | 33.8 (.3 psi) 21.0 (.7 psi) | 36.7 (.3 psi) 29.4 (.7 psi) |
| 5: 2,500 ppm crosslinker, blowing agent | 0.51 | 76,785 | 35.9 | 6.4 (.3 psi) 4.1 (.7 psi) | 18.1 (.3 psi) 8.4 (.7 psi) |
| 6: Surface crosslinked Sample 5 | 0.67 | 95,755 | 30.1 | 33.4 (.3 psi) 23.3 (.7 psi) | 34.9 (.3 psi) 28.7 (.7 psi) |

After the surfaces of the porous core polymers were crosslinked, the swell rate, gel strength and absorption under pressure substantially improved. Although the capacity was reduced, it remained within an acceptable range. When the characteristics of the superabsorbents derived from the porous core polymers are compared to those derived from the nonporous core polymers of Example 1, it is evident that incorporation of a blowing agent in the core polymer improved the swell rate of the polymer even though the swell rate, in most instances, would have declined after surface crosslinking. When compared to the nonporous core polymers of Example 2, the swell rates of the superabsorbents derived from porous core polymers were two to three times greater than those of Example 2.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

We claim:

1. A porous core superabsorbent polymer preparable by the process comprising the steps of:
    (a) providing a solution containing carboxylic acid monomers or water soluble salts thereof, and a crosslinking agent;
    (b) adding a carbonate blowing agent and a polymerization initiator, individually or in combination, to the solution to form a carbonated monomer solution;
    (c) polymerizing the carbonated monomer solution at temperatures ranging from about 0° C. to about 130° C. to form a porous core hydrogel;
    (d) chopping or grinding the porous core hydrogel into gel pieces having a particle diameter ranging from about 0.1 mm to about 5.0 cm;
    (e) drying the porous core gel pieces at temperatures ranging from about 85° C. to about 210° C. to form a porous core polymer;
    (f) grinding the pieces to form a porous core polymer having a particle size of from about 0.05 mm to about 5.0 mm;
    (g) mixing 100 parts by weight of the porous core polymer with about 0.001 to about 30 parts by weight of a surface crosslinking agent; and
    (h) reacting the porous core polymer with the surface crosslinking agent to crosslink molecular chains existing on a surface of the porous core polymer, forming the porous core superabsorbent polymer.

2. The porous core polymer of claim 1 wherein the carbonated monomer solution of step (b) is an aqueous solution containing from about 20 wt. % to about 40 wt. % (meth)acrylic acid monomers consisting essentially of from 20 wt. % to 40 wt. % (meth)acrylic acid and from 60 wt. % to 80 wt. % sodium (meth)acrylate, from about 0.05 wt. % to about 2.5 wt. % blowing agent and from about 0.005 wt. % to about 2.0 wt. % crosslinking agent.

3. The porous core polymer of claim 2 wherein the blowing agent of step (b) is a carbonate containing salt, a bicarbonate containing salt, or gaseous or solid carbon dioxide.

4. The porous core polymer of claim 3 wherein the blowing agent is selected from the group consisting of $CO_2$, $Na_2CO_3$, $K_2CO_3$, $(NH_4)_2CO_3$, $MgCO_3$, $(MgCO_3)_4 \cdot Mg(OH)_2 \cdot 5H_2O$, $CaCO_3$, $ZnCO_3$, and mixtures thereof.

5. The porous core polymer of claim 2 wherein the crosslinking agent of step (a) has at least two polymerizable double bonds, at least one polymerizable double bond and at least one functional group reactive with the acid monomers or the water soluble salts thereof, at least two functional groups reactive with the acid monomers or the water soluble salts thereof, or is a polyvalent metal compound.

6. The porous core polymer of claim 5 wherein the crosslinking agent is a bis-acrylamide, a di, tri or polyester of an unsaturated mono or poly carboxylic acid polyol, a di or tri glycidyl ether of a polyol, a multi-substituted allyl amine or mixtures thereof.

7. The porous core polymer of claim 1 wherein the polymerization initiator of step (b) is selected from the group consisting of hydrogen peroxide, sodium persulfate, azo catalysts, organic peroxides, sodium bisulfite, peracetate catalysts and mixtures thereof.

8. The porous core polymer of claim 1 wherein the carboxylic acid monomers of step (a) are selected from the group consisting of acrylic acid, methacrylic acid, acrylamide, methacrylamide, ethacrylic acid, alpha-chloroacrylic acid, alpha-cyanoacrylic acid, beta-methylacrylic acid, itaconic acid, citraconic acid, maleic acid, fumaric acid, maleic anhydride, vinyl sulfonic acids, allyl sulfonic acids, sulfoethylacrylate, sulfoethylmethacrylate, sulfopropylacrylate, sulfopropylmethacrylate, acrylamido N-methylene sulfonic acid, acrylamido-N-ethylene sulfonic acid, 2-acrylamido-2-methylpropane sulfonic acid, acrylamide, methacrylamide and mixtures thereof.

9. The porous core polymer of claim 1 wherein the process further includes the step:
(i) drying the superabsorbent polymer by application of heat.

10. The porous core polymer of claim 1 wherein the surface crosslinking agent of step (g) is an organic carbonate, a polyvalent metal, a polyquaternary amine, or a compound having at least two functional groups, per molecular unit, capable of reacting with a carboxyl group of the polymer.

11. The porous core polymer of claim 10 wherein the surface crosslinking agent is diethylene glycol, triethylene glycol, polyethylene glycol, glycerin, polyglycerin, propylene glycol, diethanolamine, triethanolamine, polyoxypropylene, oxyethylene-oxypropylene block copolymer, polyvinyl alcohol, sorbitan fatty acid ester, polyoxyethylene sorbitan fatty acid ester, trimethylol propane, pentaerythritol, sorbitol, diglycidyl ether, a polyvalent metal, alkylene carbonate, a polyquaternary amine or mixtures thereof.

12. The porous core polymer of claim 1 wherein the carbonate blowing agent is added to the monomer solution no more than five minutes before the initiator is added.

13. The porous core polymer of claim 1 wherein the initiator is added to the monomer solution no more than fifteen minutes after the carbonate blowing agent is added.

* * * * *